(12) United States Patent
Dellea et al.

(10) Patent No.: US 9,885,692 B2
(45) Date of Patent: Feb. 6, 2018

(54) METHOD FOR PRODUCING A CHROMATOGRAPHY-ENRICHMENT COLUMN

(71) Applicant: COMMISSARIAT A L'ENERGIE ATOMIQUE ET AUX ENERGIES ALTERNATIVES, Paris (FR)

(72) Inventors: Olivier Dellea, La Talaudiere (FR); Pascal Fugier, Bernin (FR); Helene Marie, Fontaine (FR); Severine Vignoud, Bernin (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 106 days.

(21) Appl. No.: 14/414,853

(22) PCT Filed: Jul. 2, 2013

(86) PCT No.: PCT/IB2013/055415
§ 371 (c)(1),
(2) Date: Jan. 14, 2015

(87) PCT Pub. No.: WO2014/013370
PCT Pub. Date: Jan. 23, 2014

(65) Prior Publication Data
US 2015/0233876 A1    Aug. 20, 2015

(30) Foreign Application Priority Data
Jul. 19, 2012 (FR) .................................... 12 57002

(51) Int. Cl.
*B05D 3/06* (2006.01)
*G01N 30/60* (2006.01)
(Continued)

(52) U.S. Cl.
CPC ......... *G01N 30/60* (2013.01); *B01D 53/0423* (2013.01); *B05D 1/005* (2013.01);
(Continued)

(58) Field of Classification Search
CPC ........ B05D 3/142; B05D 3/062; B05D 1/204; B05D 1/005
See application file for complete search history.

(56) References Cited

U.S. PATENT DOCUMENTS 6,887,384 B1 * 5/2005 Frechet .................... B01J 20/26
210/198.2
7,727,314 B1 * 6/2010 Manginell .............. G01N 1/405
422/88
(Continued)

FOREIGN PATENT DOCUMENTS

EP    2048497 A1    4/2009
FR    2903679 A1    1/2008
(Continued)

OTHER PUBLICATIONS

Bhattacharyya et al, Thermoplastic Microfluidic device for on-chip purification of nucleic acids for disposable diagnostics, Anal. Chem, 2006, vol. 78, p. 788-792.*
(Continued)

*Primary Examiner* — Dah-Wei D Yuan
*Assistant Examiner* — Nga Leung V Law
(74) *Attorney, Agent, or Firm* — Arrigo, Lee & Guttman LLP (57) ABSTRACT

The invention concerns a method for producing a chromatography-enrichment column, the method comprising the following steps: (a) depositing at least one layer of desired particles, which may be identical or different, and are intended to constitute the stationary phase, in a compact assembly, on the flat surface of a substrate; (b) crosslinking
(Continued)

the layer in at least the regions corresponding to the desired shape of the enrichment column to be obtained; (c) impregnating the layer with a light radiation-sensitive material; (d) insolating the layer obtained in step (c) so as to form insolated regions of which the shape corresponds to the desired internal shape of the enrichment column, if the light radiation-sensitive material behaves like a positive resin or to form non-insolated regions of which the shape corresponds to the desired internal shape of the enrichment column if the light radiation-sensitive material behaves like negative resin; and (e) eliminating the light radiation-sensitive material in the zones corresponding to the internal shape of the enrichment column. The invention is used in particular in the field of chemical analysis.

17 Claims, 3 Drawing Sheets

(51) Int. Cl.
    *B05D 3/14* (2006.01)
    *B05D 1/20* (2006.01)
    *B05D 1/00* (2006.01)
    *B01D 53/04* (2006.01)
    *G01N 30/02* (2006.01)

(52) U.S. Cl.
    CPC ............ *B05D 1/204* (2013.01); *B05D 3/062* (2013.01); *B05D 3/142* (2013.01); *G01N 2030/025* (2013.01)

(56) References Cited

U.S. PATENT DOCUMENTS

| | | | |
|---|---|---|---|
| 2012/0012250 A1* | 1/2012 | Ellman | ............... B01J 19/0046 156/279 |
| 2012/0113421 A1* | 5/2012 | Vignoud | ............... G01N 21/05 356/311 |
| 2015/0219605 A1 | 8/2015 | Dellea et al. | |

FOREIGN PATENT DOCUMENTS

| | | |
|---|---|---|
| JP | 2000002697 A | 1/2000 |
| WO | 2014/013368 A1 | 1/2014 |

OTHER PUBLICATIONS

Wei-Cheng Tian et al., "Multiple-Stage Microfabricted Preconcentrator-Focuser for Micro Gas Chromatography System," Journal of MIcroelectromechanical Systems, vol. 14, No. 3, pp. 498-506 (2005).
Ji, Zhenghua, et al., "Porous layer open-tubular capillary columns: preparations, applications and future directions," Journal of Chromatography A, 842 (1999) 115-142.
Office Action, U.S. Appl. No. 14/414,848, dated Nov. 1, 2016.

\* cited by examiner

METHOD FOR PRODUCING A CHROMATOGRAPHY-ENRICHMENT COLUMN

The invention relates to a process for the manufacture of a chromatography enrichment column.

The constraints brought about by increasingly strict regulations with regard to the safety of industrial plants (refineries, oil platforms, chemical plants, and the like), the need to monitor and watch over the quality of the air which we breath at our places of work or in our daily traveling involve the development of novel tools for the analysis of gases at odds with those available commercially in order to introduce substantial savings in terms of portability, sensitivity, selectivity, multiplicity of the identifiable analytes or cost.

In the field of in situ gas analysers, those available commercially do not meet all of these criteria, despite a great variety of technologies on the market (semiconducting: lack of selectivity, drift, influence of humidity; electrolytic: problem of recalibration; optical in the infrared region: size and cost, and the like).

For the analysis of complex gas mixtures, the reference method is Gas Chromatography (GC) coupled at the column outlet to a detector of TCD (thermal conductivity detector) or FID (flame ionization detector) type.

In order to complete the analyses, the chromatographs are often coupled to other analytical instruments, in particular mass spectrometry and infrared spectroscopy. However, these devices remain typical laboratory tools, bulky and very expensive. However, recent progress in micro- and nano-technologies open the way to the miniaturization of this type of high-performance and universal analyser.

The gas chromatography (GC) technique is one of the most widely used separation and analytical methods for volatile or semi-volatile compounds. In particular, in combination with mass spectrometry, it is the method of choice for the analysis of complex gas mixtures in many fields: environment, safety, the pharmaceutical industry, the food processing industry, petrochemicals, and the like.

The commonest current equipment is difficult to transport and expensive. An advantageous route to miniaturization involves the production of microcolumns etched into silicon. Apart from the advantage of the basic reduction in size, micromanufacture on silicon makes it possible to envisage novel microcolumn designs, the monolithic incorporation of several columns and/or of other functional elements (injector, detector) on the same chip, and also mass production, eventually making possible a large reduction in the costs.

The separation efficiency of the microcolumns is based on the difference in affinity of the analytes with the "stationary" phase (layer deposited on the wall of the channels) and the "mobile" phase (the carrier gas) and thus on the differential migration obtained for these analytes.

A good separating power characterizing a high-performance column involves a deposited layer which is homogeneous in composition and thickness over all the walls of the column. The deposition processes used today for silicon columns are very similar to those used for capillary columns.

Even if the separation efficiencies obtained are of the same order of magnitude as in a standard column, these processes remain chip by chip processes, that is to say processes in which the components are treated one after the other, and are limited by the non-homogeneity of the depositions, with, for example, excess thicknesses of the layers of polymers in the corners of the channels. There is plenty of room for progress, both at the performance level and at the level of reduction in the manufacturing cost, by the development of specially suited processes.

The chromatography columns generally comprise not only the analytical column itself but also an "enrichment column" which is used to concentrate, in this column, the elements to be detected and/or assayed.

The invention relates to a process for the manufacture of such an enrichment column, which is upstream of the analytical column itself.

Figure 1:
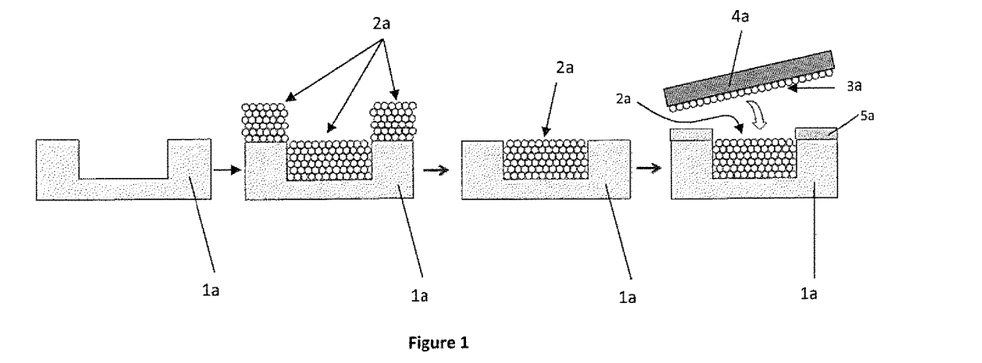
FIG. 1 shows depositing of particles as a compact assemblage in a channel and on a sealing covering cap.

The enrichment columns, when they are microcolumns on silicon, can be manufactured by the process illustrated diagrammatically in FIG. 1.

As is seen in FIG. 1, the shape of the enrichment column to be obtained is etched into a substrate, denoted 1a in FIG. 1, generally made of silicon.

Subsequently, at least one layer, denoted 2a in FIG. 1, of particles as a compact assemblage is deposited.

Generally, a multilayer deposition, that is to say a deposition of several layers, as illustrated in FIG. 1, is carried out in order to completely fill the internal cavity of the column with the stationary phase.

The particles at the surface of the rims of the substrate 1a made of silicon are subsequently removed.

The microchannel is subsequently sealed with a covering cap, denoted 4a in FIG. 1, comprising, on the sealed face on the structure obtained, a layer 3a of particles. The particles constituting the layers 2a and 3a can be identical or different. Even within the same layer, there may be identical or different particles.

The sealing can be carried out by adhesive bonding with adhesive, denoted 5a in FIG. 1.

However, with this process, the homogeneity of the assemblage of the microparticles is not guaranteed due to the surface topology.

The invention is targeted at overcoming the problems of the processes for the manufacture of the chromatography-enrichment columns of the prior art.

The process of the invention can be applied to any type of substrate and does not require the etching of this same substrate. By this method, low-cost components on plastic can be envisaged.

It makes it possible to have particles homogeneously distributed in the enrichment channel. Furthermore, it makes it possible to construct the component layer by layer and thus to combine particles having different natures, dimensions and surface activations.

In this approach, as the substrate is not etched, the great majority of the techniques for deposition of particles as a compact assemblage are compatible in carrying out the particle deposition. In the case of an etched substrate, deposition techniques such as that of spin deposition cannot be employed because of the surface topology related to the etchings.

To this end, the invention provides a process for the manufacture of a chromatography-enrichment column, characterized in that it comprises the following steps:

a) deposition of at least one layer of the desired particles, which are identical or different and which are intended to form the stationary phase, as a compact assemblage on the flat surface of a support, b) crosslinking of said layer in at least the regions corresponding to the desired shape of the enrichment column to be obtained, c) impregnation of said layer with a material sensitive to light radiation, d) insolation of the layer obtained in step c) in order to form insolated regions, the shape of which corresponds to the internal shape desired for the enrichment column, when the material sensitive to light radiation behaves as a positive resin, or in order to form non-insolated regions, the shape of which corresponds to the internal shape desired for the enrichment column, when the material sensitive to light radiation behaves as a negative resin, and e) removal of the material sensitive to light radiation in the regions corresponding to the internal shape of the enrichment column.

In a first embodiment of the process of the invention, step b) is carried out after step c) and the particles of the layer have a functional group which is photocrosslinkable at a wavelength $\lambda 1$ and the material sensitive to light radiation is a material sensitive to light radiation having a wavelength $\lambda 2$ identical to or different from the wavelength $\lambda 1$.

Preferably, the process of the invention additionally comprises, before step a), a step of activation of said surface of the substrate, preferably by $O_2$ plasma, UV radiation, a mixture of sulfuric acid and of hydrogen peroxide, or ozone.

In the process of the invention, preferably, said particles have a mean diameter, measured by a Zetasizer® or Nanosizer® or scanning electron microscope, of between 50 nm and 500 µm inclusive.

Preferably again, in the process of the invention, the thickness of the layer or the total thickness of the layers of particles as a compact assemblage is comprised between 50 and 700 µm inclusive.

Also preferably, the particles are particles made of a metal oxide, of a metal, of a polymer, of a polysaccharide or of a ceramic or mixtures of these. The particles are preferably chosen from the group consisting of silica, titanium dioxide, alumina, latex, polydimethylsiloxane (PDMS), gold, copper and the mixtures of these.

These particles can in addition be functionalized, for example in order to be specific and/or selective for the analyte to be identified.

Step a) can be carried out by the Langmuir-Blodgett method, or by the Langmuir-Schaefer method, or by Marangoni self-assembling, or by the vortical surface method, or by floating-transferring, or by dip coating, or by spin coating.

In a first embodiment of the process of the invention, the photosensitive material behaves as a positive resin sensitive to radiation with a wavelength $\lambda 2$ of between 150 and 700 nm inclusive.

In a second embodiment of the process of the invention, the photosensitive material behaves as a negative resin sensitive to radiation with a wavelength $\lambda 2$ of between 150 and 700 nm inclusive.

In a third embodiment of the process of the invention, the photosensitive material is obtained by a sol-gel process and is sensitive to light radiation with a wavelength $\lambda 2$ of between 150 and 700 nm inclusive.

In the first embodiment of the process of the invention, the particles are functionalized with a functional group sensitive to light radiation preferably having a wavelength $\lambda 1$ of between 150 and 700 nm inclusive.

Step c) of impregnation of the layers of particles as a compact assemblage can be carried out by spin deposition of the material sensitive to light radiation on said layers or by immersion of the substrate coated with said layers in the material photosensitive to light radiation.

Preferably, the process of the invention additionally comprises, after step e), a step of covering and sealing the structure obtained with a covering cap.

In the process of the invention, the substrate can be rigid or flexible and made of metal oxide, of metal, of ceramic or of polymer.

Figure 2:
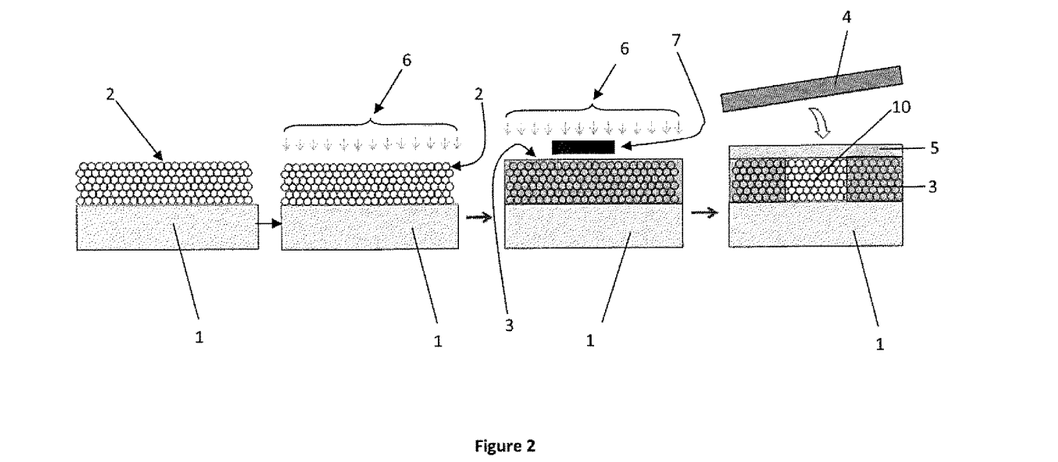
FIG. 2 shows the process for the manufacture of a chromatography-enrichment column according to the invention.

A better understanding of the invention will be obtained and other characteristics and advantages of the latter will become more clearly apparent on reading the explanatory description which follows and which is made with reference to FIG. 2, which presents, in diagrammatic form, the various steps of the process for the manufacture of a chromatography-enrichment column according to the invention.

Overall, the process of the invention consists in depositing, on the surface of a substrate (an unstructured substrate, that is to say on a flat surface which has not been subjected to an etching step but is optionally activated), a multilayer structure composed of compact films of particles as a compact assemblage (also known as "colloidal crystal") over a thickness sufficient to form the enrichment microcolumns or preconcentrators.

The following steps of the process depend on the final object to be achieved and consist briefly in impregnating the layer as a compact assemblage with a photosensitive material (the material sensitive to light radiation) and in carrying out photolithography steps in order to create microchannels. Depending on the thickness of the multilayer structure to be insolated, the insolation is carried out under a mask or with commercial laser equipment designed specifically for the insolation of resins deposited as a thick layer (up to 1000 µm for the laser process). In order to finish, a sealing step is carried out.

Thus, the first step of the process of the invention is a step of formation of a layer, denoted 2 in FIG. 2, of particles as a compact assemblage on the surface of a substrate, denoted 1 in FIG. 2.

The particles used typically have a mean diameter, measured by Zetasizer®, by Nanosizer® or by scanning electron microscopy, within the interval from 50 nm to 500 µm inclusive.

Generally, several layers 2 are deposited on the substrate 1.

The substrate 1 can be made of a metal oxide, of a ceramic, of a polymer material or of metal, such as silicon.

When the substrate has to be flexible, use will preferably be made of a substrate made of a polymer, such as poly (ethylene terephthalate) (PET), poly(ethylene naphthalate) (PEN) or a polycarbonate (PC).

As can be seen in FIG. 2, the layer 2 of particles as a compact assemblage is formed on a flat surface of the substrate, that is to say on an unstructured substrate, in which the shape of the enrichment column has not yet been formed.

Subsequently, either the particles making up this layer 2 are crosslinked, selecting only the regions of the layer 2 corresponding to the internal shape desired for the enrichment column, or the entire layer 2 is crosslinked, in order to "fix" the network of particles. It is preferable to crosslink the entire layer 2 in order to limit the risks of having a non-homogeneous distribution of the impregnation material.

When only certain regions of the layer 2 are selected, the particles have, at the surface, a functional group which is crosslinkable by a light ray having a wavelength λ1 of between 150 and 700 nm inclusive.

When no region is selected, the insolation is homogenous over the surface; there is no mask during the insolation.

The layer 2 is then impregnated with a material sensitive to light radiation, denoted 6 in FIG. 2.

When only certain regions of the particles of the layer 2 have been crosslinked beforehand, then this material has to be sensitive to light radiation 6 having a wavelength λ2 identical to or different from λ1.

This wavelength λ2 is generally comprised between 150 and 700 nm inclusive.

The impregnated layer, denoted 3 in FIG. 2, thus obtained is then insolated, either through a mask or in localized fashion by laser, in order to crosslink the impregnation material and to form the microchannels.

When the impregnation photosensitive material behaves as a positive resin, use will be made of a mask, denoted 7 in FIG. 2, comprising regions transparent to light radiation 6, these transparent regions outlining the shape of the microchannel constituting the desired enrichment column.

It will also be possible to use a laser beam to irradiate only in the regions outlining the shape of the desired enrichment column.

When the impregnation sensitive material behaves as a positive resin, use will be made either of a mask comprising regions transparent to light radiation 6, these regions having the shape desired for the enrichment column to be obtained, or irradiation will be carried out with a laser beam, these regions having the shape desired for the enrichment column to be obtained.

The material sensitive to light radiation 6 will then be removed from the regions corresponding to the shape desired for the enrichment column to be obtained.

Finally, the structure thus obtained will be sealed with a covering cap, denoted 4 in FIG. 2.

This covering cap 4 can comprise one or more layers of the desired particles on its face facing the layer 2 when the adhesive 5 is distributed uniformly over the stack of the layers. This implies that the adhesive is compatible with the functionalizations and does not impregnate the layers of particles forming the channel In the contrary case, the adhesive must be distributed solely in regions outside the channels and the excess thickness generated by its presence may require depositing one or more layers of particles on the covering cap.

The sealing can be carried out, for example, using an adhesive, denoted 5 in FIG. 2.

The particles can be made of metal oxide, preferably of silica, of a ceramic, preferably of titanium dioxide or alumina, of polymers, preferably, of latex or of polydimethoxysilane or polysaccharides, or of metal, preferably gold or copper.

The multilayer deposition of particles as a compact assemblage can be carried out by stacking the layers one after the other or directly and collectively. The diameter for particles used is typically within a range from 50 nm to 500 μm inclusive. In the present text, the mean diameter is measured by Nanosizer®, Zetasizer® or scanning electron microscopy. The thickness of the multilayer structure is from 50 μm to 700 μm inclusive.

The techniques which make it possible to produce a monolayer of particles as a compact assemblage are, for example:

The Langmuir-Blodgett method: This technique comprises a carrier liquid (for example water) in which the "target" substrate onto which the monolayer of particles has to be transferred is immersed beforehand in the vertical position. The particles are distributed at the surface of the liquid, over which they disperse. A mechanical device (known as barrier) is then set in motion in order to gradually reduce the surface area occupied by the particles in order to compress them. When the compact film is formed, the substrate is set in motion in order to deposit the film at its surface by capillary action. The barrier has to accompany this drawing movement in order to keep the particles compressed [1,2].

The Langmuir-Schaefer method: The principle of the Langmuir-Schaefer technique is basically the same as that used in the Langmuir-Blodgett case, the only difference being that the substrate is positioned horizontally [1].

Self-assembling by the Marangoni mechanism: The method of self-assembling by the Marangoni mechanism [3,4] is similar to those presented above. Specifically, while the deposition step is basically identical to the Langmuir-Blodgett method, the mode of assembling the particles is different: the particles, rendered hydrophobic, are dissolved in ethanol and dispersed at the surface of the water. The difference in surface tension between the ethanol (22 dyn/cm) and the water (73 dyn/cm) creates a surface flow, known as Marangoni flow, which results in a variation in the thickness of the ethanol film at the surface of the water. The agitation brought about by this phenomenon makes possible the organization of the particles among themselves.

The vortical surface method: The vortical surface method [5] consists in creating a vortex (using a magnetic stirrer) at the surface of the water and in dispersing the hydrophobic particles over this vortex. As the particles are hydrophobic, they remain at the surface of the vortex. Thus, the particles become organized among themselves by virtue of compression. The deposition on a substrate is carried out according to the Langmuir-Blodgett method.

Floating-transferring: the substrate is immersed beforehand in the liquid and the particles, for example of polystyrene, are deposited at the surface of the water; the particles are subsequently coagulated by addition of sodium dodecyl sulfate and the film is deposited by withdrawing the substrate from the water [6,7].

Dip coating.

Spin coating.

Spray coating.

The drop-coating technique can be used to directly produce the multilayer structure [8,9]: a colloidal solution is deposited at the surface of the hydrophilic substrate and slow evaporation of the solvent results in an ordered structure of particles. This technique is difficult to control over large surface areas and, in the case where particles of different natures or functionalizations are used, it does not make it possible to control the composition of the layers forming the multilayer structure.

In order to promote the deposition of the particles, a pretreatment of the surface of the substrate is possible by $O_2$ plasma, UV radiation, a Piranha solution (mixture of $H_2SO_4$ and $H_2O_2$) or ozone, making it possible simultaneously to remove possible physically absorbed organic matter and to generate silanol groups at the surfaces (for substrates made of silicon) in order to obtain optimum fixing of the functional molecules.

This step is optional.

The particles used, in the case where their crosslinking is carried out before the impregnation with the material sensitive to light radiation 6, have to be functionalized with a functional group which is crosslinkable at a wavelength λ1.

The particles can also be functionalized with many other molecules as a function, for example, of the detected analyte.

Also, after the production of a multilayer structure by one of the abovementioned techniques, it is necessary to stabilize the system. This point can be settled by the grafting, to the particles, of functional groups which make possible the crosslinking of the particles among themselves. The functionalized particles have to be crosslinkable by UV radiation, the thermal route, and the like, in order to form a compact three-dimensional network.

It should be emphasized that it is necessary to preserve all the active functional groups (microchannels) of the enrichment column making possible the adsorption of the gases or fluids.

Furthermore, the functionalized particles have to be compatible with the photosensitive material (material sensitive to light radiation 6) making possible the production of the component.

The column is subsequently obtained by a photolithography process.

Photolithography is a conventional process widely used in microelectronics to manufacture micron-scale systems. The steps of the photolithography process begin by the application of a photosensitive material and the formation of a thin layer on the surface of a substrate (silicon, polymers, and the like).

After thermal annealing, this sensitive layer is subsequently exposed, partially, to light radiation. During this second step of the process, the use of a mask, composed of regions opaque and transparent to light radiation, makes it possible to define the geometric pattern which it is desired to reproduce on the substrate.

The principle of photolithography is based on the ability of photosensitive materials to experience a change in their solubility as a function of the amount of light radiation absorbed.

Several photosensitive materials can be envisaged and have to be selected according to their compatibilities with the functionalized particles:

Resins:
positive resins, the illuminated part of which is removed during the development, subsequent to the decomposition (photolysis) of the photosensitive portion of the photoactive compound (for example, DiazoNaphthoQuinone DNQ) which they comprise, and negative resins, which, on the contrary, crosslink under the effect of the radiation and the illuminated parts of which will be insoluble in the solvents used during the development.

Sol-gels, which can be photosensitive materials which behave both as a positive resin and as a negative resin, depending on the materials of which they are composed.

The principle of the sol-gel process, sometimes known as "soft chemistry", is based on the use of a sequence of hydrolysis-condensation reactions, at moderate temperature, in order to prepare networks of oxides which can, in their turn, be heat treated.

Organic-inorganic sol-gel hybrids make it possible to obtain chemically homogenous microstructures. The syntheses of organic-inorganic hybrid materials are widely described in the literature. Sol-gels based on MAPTMS (MethAcryloyloxyPropylTriMethoxySilane) and on ZPO (Zirconium PropOxyde) are examples of such materials which can be used in the process of the invention. A photoinitiator (such as Irgacure® 369 or 189 from CIBA) added to the solution confers, on this hybrid, the photosensitive properties of a negative resin and the variation in the concentration of ZPO makes it possible to vary the refractive index between 1.48 and 1.52.

Figure 3:
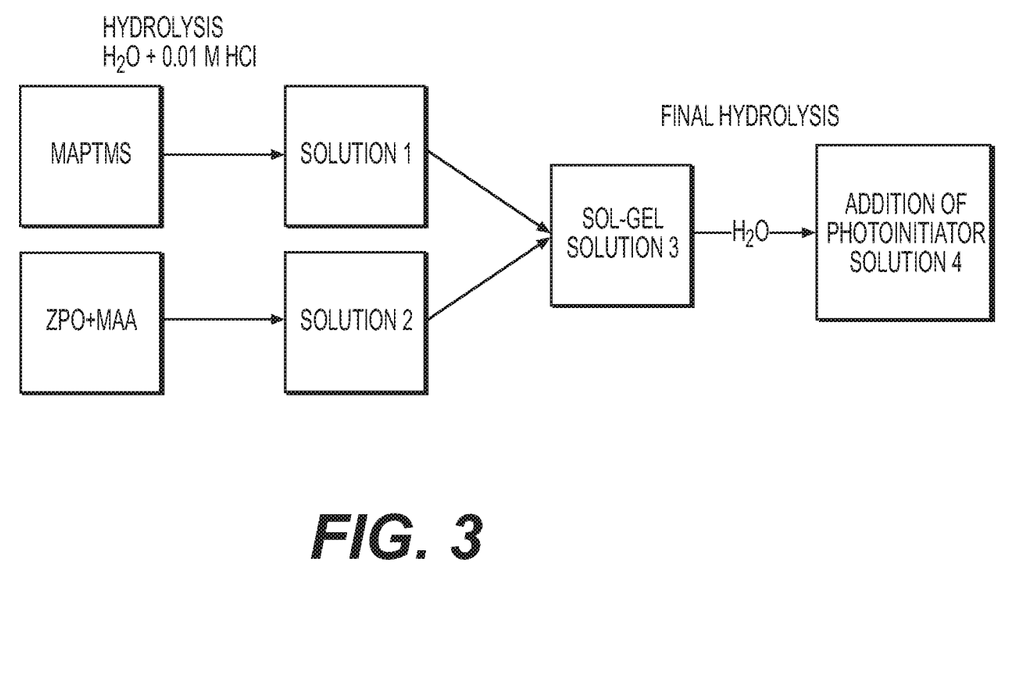
FIG. 3 illustrates the principal of the preparation of the sol-gel hybrid.

The principle for the preparation of the sol-gel hybrid [10] is represented in the scheme shown in FIG. 3.

Figure 4:
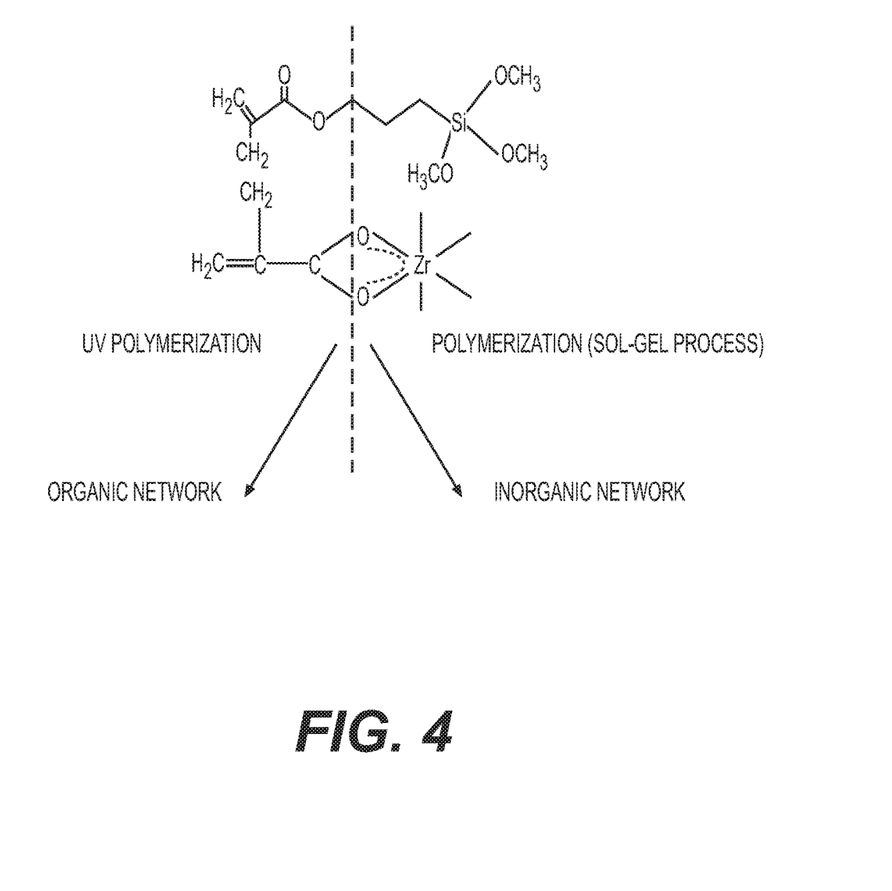
FIG. 4 presents a diagrammatical representation of an inorganic network and an organic network.

The final material comprises an inorganic network and an organic network. The inorganic network is obtained by hydrolysis and polycondensation of the alkoxide groups, while the organic network is created by polymerization of the double bonds, mainly C=C double bonds, under the action of the ultraviolet photons.

The networks of the sol-gel hybrid material [11] are represented in FIG. 4.

Generally, the photosensitive materials are spread over the substrate by spin coating. Another solution consists in impregnating the structure by slowly and gradually immersing the substrate. The impregnation material fills the interstices between the particles via capillary forces.

In order to initiate the crosslinking reaction, the photosensitive material has to undergo exposure to UV light. In this approach, the layer to be insolated is regarded by a person skilled in the art as thick (>10 μm). Appliances are currently on sale which make it possible to insolate such thicknesses by using the masking technique (for example: Q7000 Mask Aligner®, supplier Neutronix-Quintel) or by writing by direct laser writing (for example: DILASE® appliance, supplier Kloé). The irradiation dose is adjusted as a function of the thickness of the film. It is the product of the irradiation time and of the intensity of the UV light.

The insolated photosensitive material is subsequently developed in order to reveal the microstructures. This phase is based on the dissolution of the photosensitive materials in a solvent, or by successive rinsing operations with butanol and isopropanol for the sol-gel hybrids.

Several methods exist for the development of the resins. The commonest is immersion with stirring of the bath but evaporation may also be encountered.

The developer and the development process must not inhibit the functionalization of the particles making possible the separation of the gases and fluids.

An annealing step of densification and of relaxation of the stresses can also be carried out. This step is not necessarily carried out. However, the annealing makes it possible to activate the end of the crosslinking of the network formed by the photosensitive material impregnating the layers of particles and forming the walls of the microcolumn. This annealing makes it possible to relax the stresses and to stabilize the final structure.

Finally, for the sealing of the structure obtained, generally, the industrial sealing of the microstructures is carried out according to different routes:

Liquid route: SiPix Imaging Inc. has developed several novel methods [12,13] for closing the micropits used in electrophoretic screens, all based on the principle of immiscibility between two liquids.

Solid route: Pressure-sensitive adhesives (PSAs) are elastomeric viscoelastic materials which can adhere strongly to a solid surface on applying a low pressure and a low contact time. The incorporation of oligomers sensitive to UV radiation and of photoinitiators in the formulation of the adhesives makes it possible to obtain UV-crosslinkable PSA adhesives [14]. With regard to hot-melt adhesives, they are deposited in the molten state (low viscosity) and their cohesion is provided during the cooling.

REFERENCES

[1] Somobrata Acharya, Jonathan P. Hill and Katsuhiko Ariga, "Soft Langmuir—Blodgett Technique for Hard Nanomaterials", Adv. Mater., 2009, 21, 2959-2981.
[2] Maria Bardosova, Martyn E. Pemble, Ian M. Povey and Richard H. Tredgold, "The Langmuir-Blodgett Approach to Making Colloidal Photonic Crystals from Silica Spheres", Adv. Mater., 2010, 22, 3104-3124.
[3] Masahiro Shishido and Daisuke Kitagawa, "Preparation of ordered mono-particulate film from colloidal solutions on the surface of water and continuous transcription of film to substrate", Colloids and Surfaces A: Physicochem. Eng. Aspects, 311 (2007), 32-41.
[4] Sanjib Biswas and Lawrence T. Drzal, "A Novel Approach to Create a Highly Ordered Monolayer Film of Graphene Nanosheets at the Liquid-Liquid Interface", Nano Lett., Vol. 9, No. 1, 2009.
[5] Feng Pan, Junying Zhang, Chao Cai and Tianmin Wang, "Rapid Fabrication of Large-Area Colloidal Crystal Monolayers by a Vortical Surface Method", Langmuir, 2006, Vol. 22, No. 17, pp 7101-7104.
[6] Y. J. Zhang, W. Li and K. J. Chen, "Application of two-dimensional polystyrene arrays in the fabrication of ordered silicon pillars", Journal of Alloys and Compounds, 450 (2008), 512-516.
[7] J. Rybczynski, U. Ebels and M. Giersig, "Large-scale, 2D arrays of magnetic nanoparticles", Colloids and Surfaces A: Physicochem. Eng. Aspects, 219 (2003), 1-6.
[8] D. Nagao, R. Kameyama and H. Matsumoto, "Single- and multi-layered patterns of polystyrene and silica particles assembled with a simple dip-coating", Colloid and Surfaces A: Physiochem. Eng. Aspects, 2008, Vol. 317, pp 722-729.
[9] S. Rakers, L. F. Chi and H. Fuchs, "Influence of the Evaporation Rate on the Packing Order of Polydisperse Latex Monofilms", Langmuir, 1997, 13, 7121-7124.
[10] V. Conedera, N. Fabre and H. Camon "Les matériaux élaborés par sol-gel et leur utilisation en micro Technologies [Materials prepared by the sol-gel process and their use in microtechnologies]", LAAS Report No. 02217 (2002).
[11] P. Coudray, P. Etienne and Y. Moreau, "Integrated optics based on organo-mineral materials", Invited paper of European materials conference-Strasbourg (1999).
[12] R. C. Liang, M. Chan-Park, S. C-J, Tseng, Z-A G. Wu and H. M. Zang, "Electrophoretic display", Patent Publication No. WO 01/67171 A1, (2001).
[13] R. C. Liang, Z-A. G. Wu and H. M. Zang, "Manufacturing process for multi-layer color displays", Patent Publication No. WO2004/051353 (2004).
[14] T. Ozawa, S. Ishiwata and Y. Kano, "Adhesive Properties of Ultraviolet Curable Pressure-Sensitive Adhesive Tape for Semiconductor Processing (I)-Interpretation via Rheological Viewpoint", Furukawa Review, 20, 83 (2001).

The invention claimed is:

1. A process for manufacturing a chromatography enrichment column, characterized in that it comprises the following steps:
    a) providing a support comprising a flat outer surface (1), wherein the support does not comprise a channel,
    b) depositing at least one layer (2) of the desired particles, which can be identical to or different from one another, as a compact assemblage on the flat outer surface of the support (1),
    c) crosslinking the at least one layer in at least the regions corresponding to the desired shape of the column to be obtained,
    d) impregnating the layer with a material sensitive to light radiation in order to obtain an impregnated layer,
    e) insolating the layer obtained in step d) in order to form insolated regions, the shape of which corresponds to the internal shape of the desired enrichment column, when the material sensitive to light radiation behaves as a positive resin, or in order to form non-insolated regions, the shape of which corresponds to the internal shape desired for the enrichment column, when the material sensitive to light radiation behaves as a negative resin, and f) removing the material sensitive to light radiation in the region of the layer which corresponds to the internal shape desired for the enrichment column, to thereby provide the chromatography enrichment column.

2. The process as claimed in claim 1, characterized in that step c) is carried out after step d) and in that the particles of the layer (2) have a functional group which is photocrosslinkable at a wavelength $\lambda 1$ and the material sensitive to light radiation (6) is a material sensitive to light radiation having a wavelength $\lambda 2$ identical to or different from the wavelength $\lambda 1$.

3. The process as claimed in claim 1, characterized in that it additionally comprises, before step b), a step of activation of said surface of the substrate (1) by O2 plasma, UV radiation, a mixture of sulfuric acid and of hydrogen peroxide, or ozone.

4. The process as claimed in claim 1, characterized in that said particles have a mean diameter is from 50 nm to 500 µm inclusive.

5. The process as claimed in claim 1, characterized in that the thickness of the layer (2) or the total thickness of the layers (2) is from 50 to 700 µm inclusive.

6. The process as claimed in claim 1, characterized in that the particles are particles made of a metal oxide, of a metal, of a polysaccharide, of a ceramic or a mixture of these.

7. The process as claimed in claim 1, characterized in that step a) is carried out by the Langmuir-Blodgett method, or by the Langmuir-Schaefer method, or by Marangoni self-assembling, or by the vortical surface method, or by floating-transferring, or by dip coating, or by spin coating.

8. The process as claimed in claim 1, characterized in that the photosensitive material behaves as a positive resin sensitive to radiation with a wavelength $\lambda 2$ of from 150 to 700 nm inclusive.

9. The process as claimed in claim 1, characterized in that the photosensitive material behaves as a negative resin sensitive to radiation with a wavelength $\lambda 2$ of from 150 to 700 nm inclusive.

10. The process as claimed in claim 1, characterized in that the photosensitive material is obtained by a sol-gel process.

11. The process as claimed in claim 2, characterized in that the particles are functionalized with a functional group sensitive to light radiation with a wavelength $\lambda 1$ of from 150 to 700 nm inclusive.

12. The process as claimed in claim 1, characterized in that step d) of impregnation of the layer (2) is carried out by spin deposition of the material sensitive to light radiation (6) on the layer (2) or by immersion of the substrate (1) coated with the layer (2) in the material photosensitive to light radiation (6).

13. The process as claimed in claim 1, characterized in that it additionally comprises, after step f), a step of covering and sealing the layer (2) of the structure obtained with a covering cap (4).

14. The process as claimed in claim 1, characterized in that the substrate (1) is made of a metal oxide, of a metal, of a polymer, of a polysaccharide or of a ceramic.

15. The process as claimed in claim 1, characterized in that the substrate (1) is made of silicon.

16. The process of claim 6, characterized in that the particles are particles made of a material chosen from silica, titanium dioxide, alumina, latex, polydimethoxysilane, gold, copper and the mixtures thereof and are optionally functionalized.

17. The process of claim 6, characterized in that the particles are functionalized.

* * * * *